United States Patent
Rao et al.

(10) Patent No.: US 10,964,431 B2
(45) Date of Patent: *Mar. 30, 2021

(54) TECHNIQUE FOR LINKING ELECTRODES TOGETHER DURING PROGRAMMING OF NEUROSTIMULATION SYSTEM

(71) Applicant: Boston Scientific Neuromodulation Corporation, Valencia, CA (US)

(72) Inventors: Prakash Rao, Philadelphia, PA (US); Sridhar Kothandaraman, Valencia, CA (US); Christopher Britton Gould, San Carlos, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 67 days.

This patent is subject to a terminal disclaimer.

(21) Appl. No.: 16/242,863

(22) Filed: Jan. 8, 2019

(65) Prior Publication Data

US 2019/0148009 A1    May 16, 2019

Related U.S. Application Data

(63) Continuation of application No. 15/361,259, filed on Nov. 25, 2016, now Pat. No. 10,199,125, which is a
(Continued)

(51) Int. Cl.
*A61N 1/372* (2006.01)
*G16H 40/63* (2018.01)
(Continued)

(52) U.S. Cl.
CPC ........... *G16H 40/63* (2018.01); *A61N 1/0551* (2013.01); *A61N 1/3605* (2013.01);
(Continued)

(58) Field of Classification Search
CPC ................ A61N 1/0551; A61N 1/3605; A61N 1/36185; A61N 1/37211; A61N 1/37247; G06F 19/00; G16H 40/63
See application file for complete search history.

(56) References Cited

U.S. PATENT DOCUMENTS

| | | |
|---|---|---|
| 5,643,330 A | 7/1997 | Holsheimer et al. |
| 6,052,624 A | 4/2000 | Mann |

(Continued)

FOREIGN PATENT DOCUMENTS

| | | |
|---|---|---|
| EP | 2780078 B1 | 5/2017 |
| WO | WO-2007097859 A1 | 8/2007 |

(Continued)

OTHER PUBLICATIONS

"U.S. Appl. No. 13/679,551, Advisory Action dated Dec. 11, 2013", 3 pgs.
(Continued)

*Primary Examiner* — George Manuel
(74) *Attorney, Agent, or Firm* — Schwegman Lundberg & Woessner, P.A,

(57) ABSTRACT

An external control device for use with a neurostimulator coupled to a plurality of electrodes capable of conveying electrical stimulation energy into tissue in which the electrodes are implanted. The external control device comprises a user interface including at least one control element, a processor configured for independently assigning stimulation amplitude values to a first set of the electrodes, for linking the first set of electrodes together in response to the actuation of the at least one control element, and for preventing the stimulation amplitude values of the first linked set of electrodes from being varied relative to each other, and output circuitry configured for transmitting the stimulation amplitude values to the neurostimulator.

20 Claims, 10 Drawing Sheets

Related U.S. Application Data continuation of application No. 13/679,551, filed on Nov. 16, 2012, now Pat. No. 9,504,838.

(60) Provisional application No. 61/561,760, filed on Nov. 18, 2011.

(51) Int. Cl.
 *A61N 1/36* (2006.01)
 *A61N 1/05* (2006.01)
 *G06F 19/00* (2018.01)

(52) U.S. Cl.
 CPC ...... *A61N 1/36185* (2013.01); *A61N 1/37211* (2013.01); *A61N 1/37247* (2013.01); *G06F 19/00* (2013.01)

(56) References Cited

U.S. PATENT DOCUMENTS

| | | | |
|---|---|---|---|
| 6,236,892 B1 | 5/2001 | Feler | |
| 6,393,325 B1 | 5/2002 | Mann et al. | |
| 6,516,227 B1 | 2/2003 | Meadows et al. | |
| 6,584,724 B1 | 7/2003 | Le Blanc | |
| 6,609,032 B1 | 8/2003 | Woods et al. | |
| 6,622,048 B1 | 9/2003 | Mann et al. | |
| 6,895,280 B2 | 5/2005 | Meadows et al. | |
| 6,909,917 B2 | 6/2005 | Woods et al. | |
| 6,993,384 B2 | 1/2006 | Bradley et al. | |
| 7,047,079 B2 | 5/2006 | Erickson | |
| 7,171,272 B2 | 1/2007 | Blamey et al. | |
| 7,174,215 B2 | 2/2007 | Bradley | |
| 7,184,837 B2 | 2/2007 | Goetz | |
| 7,239,920 B1 | 7/2007 | Thacker et al. | |
| 7,263,402 B2 | 8/2007 | Thacker et al. | |
| 7,489,970 B2 | 2/2009 | Lee et al. | |
| 7,519,431 B2 | 4/2009 | Goetz et al. | |
| 7,555,346 B1 | 6/2009 | Woods et al. | |
| 7,930,030 B2 | 4/2011 | Woods et al. | |
| 8,121,701 B2 | 2/2012 | Woods et al. | |
| 8,265,762 B2 | 9/2012 | Woods et al. | |
| 8,401,658 B2 | 3/2013 | Woods et al. | |
| 8,554,331 B2 | 10/2013 | Gerber et al. | |
| 8,660,653 B2 | 2/2014 | Kothandaraman | |
| 8,805,524 B2 | 8/2014 | Woods et al. | |
| 8,909,350 B2 | 12/2014 | Lee | |
| 8,977,360 B2 | 3/2015 | Kim et al. | |
| 9,002,460 B2 | 4/2015 | Parker | |
| 9,002,461 B2 | 4/2015 | Walker et al. | |
| 9,008,786 B2 | 4/2015 | Neal et al. | |
| 9,014,813 B2 | 4/2015 | Foutz et al. | |
| 9,050,473 B2 | 6/2015 | Woods et al. | |
| 9,504,838 B2 | 11/2016 | Rao et al. | |
| 9,789,252 B2 | 10/2017 | Gerber et al. | |
| 10,199,125 B2 | 2/2019 | Rao et al. | |
| 2001/0034542 A1 | 10/2001 | Mann | |
| 2003/0195582 A1 | 10/2003 | Mann | |
| 2004/0116978 A1 | 6/2004 | Bradley | |
| 2005/0209655 A1 | 9/2005 | Bradley et al. | |
| 2005/0245681 A1 | 11/2005 | McGrath et al. | |
| 2007/0073357 A1 | 3/2007 | Rooney et al. | |
| 2007/0156207 A1 | 7/2007 | Kothandaraman et al. | |
| 2007/0179579 A1 | 8/2007 | Feler et al. | |
| 2007/0213789 A1 | 9/2007 | Nolan et al. | |
| 2007/0265679 A1 | 11/2007 | Bradley et al. | |
| 2007/0265681 A1 | 11/2007 | Gerber et al. | |
| 2008/0071625 A1 | 3/2008 | Arumugam | |
| 2008/0215119 A1 | 9/2008 | Woods et al. | |
| 2008/0243196 A1 | 10/2008 | Libbus et al. | |
| 2009/0112282 A1 | 4/2009 | Witt et al. | |
| 2009/0149917 A1* | 6/2009 | Whitehurst ........ A61N 1/36017 607/59 |
| 2009/0240302 A1 | 9/2009 | Woods et al. | |
| 2010/0010566 A1 | 1/2010 | Thacker et al. | |
| 2010/0121409 A1 | 5/2010 | Kothandaraman et al. | |
| 2011/0257707 A1 | 10/2011 | Kothandaraman | |
| 2012/0109230 A1 | 5/2012 | Kothandaraman et al. | |
| 2012/0130448 A1 | 5/2012 | Woods et al. | |
| 2013/0131760 A1 | 5/2013 | Rao et al. | |
| 2014/0324124 A1 | 10/2014 | Woods et al. | |
| 2015/0039048 A1 | 2/2015 | Woods et al. | |
| 2017/0091405 A1 | 3/2017 | Rao et al. | |
| 2017/0120043 A1 | 5/2017 | John | |
| 2017/0120056 A1 | 5/2017 | Woods et al. | |

FOREIGN PATENT DOCUMENTS

| | | |
|---|---|---|
| WO | WO-2008070140 A2 | 6/2008 |
| WO | WO-2013075019 | 5/2013 |

OTHER PUBLICATIONS

"U.S. Appl. No. 13/679,551, Appeal Brief filed Feb. 4, 2014", 12 pgs.
"U.S. Appl. No. 13/679,551, Appeal Decision dated Jun. 17, 2016", 6 pgs.
"U.S. Appl. No. 13/679,551, Examiner's Answer dated Mar. 20, 2014", 7 pgs.
"U.S. Appl. No. 13/679,551, Final Office Action dated Oct. 28, 2013", 8 pgs.
"U.S. Appl. No. 13/679,551, Non Final Office Action dated Aug. 5, 2013", 6 pgs.
"U.S. Appl. No. 13/679,551, Notice of Allowance dated Jul. 26, 2016", 5 pgs.
"U.S. Appl. No. 13/679,551, Reply Brief filed May 3, 2014", 3 pgs.
"U.S. Appl. No. 13/679,551, Response filed Oct. 17, 2013 to Non Final Office Action dated Aug. 5, 2013", 8 pgs.
"U.S. Appl. No. 13/679,551, Response filed Dec. 5, 2013 to Final Office Action dated Oct. 28, 2013", 9 pgs.
"U.S. Appl. No. 15/361,259, Advisory Action dated Jan. 30, 2018", 3 pgs.
"U.S. Appl. No. 15/361,259, Final Office Action dated Nov. 22, 2017", 8 pgs.
"U.S. Appl. No. 15/361,259, Non Final Office Action dated Apr. 24, 2018", 10 pgs.
"U.S. Appl. No. 15/361,259, Non Final Office Action dated Jul. 11, 2017", 7 pgs.
"U.S. Appl. No. 15/361,259, Notice of Allowance dated Sep. 25, 2018", 5 pgs.
"U.S. Appl. No. 15/361,259, Preliminary Amendment filed Dec. 29, 2016", 7 pgs.
"U.S. Appl. No. 15/361,259, Response filed Jan. 16, 2018 to Final Office Action dated Nov. 22, 2017", 9 pgs.
"U.S. Appl. No. 15/361,259, Response filed Jul. 18, 2018 to Non Final Office Action dated Apr. 24, 2018", 10 pgs.
"U.S. Appl. No. 15/361,259, Response filed Nov. 8, 2017 to Final Office Action dated Jul. 11, 2017", 8 pgs.
"European Application Serial No. 12795691.0, Office Action dated Jul. 25, 2014", 2 pgs.
"European Application Serial No. 12795691.0, Response filed Feb. 3, 2015 to Office Action dated Jul. 25, 2014", 2 pgs.
"International Application Serial No. PCT/US2012/065668, International Preliminary Report on Patentability dated May 30, 2014", 6 pgs.
"International Application Serial No. PCT/US2012/065668, International Search Report dated Mar. 27, 2013", 4 pgs.
"International Application Serial No. PCT/US2012/065668, Written Opinion dated Mar. 27, 2013", 5 pgs.

\* cited by examiner

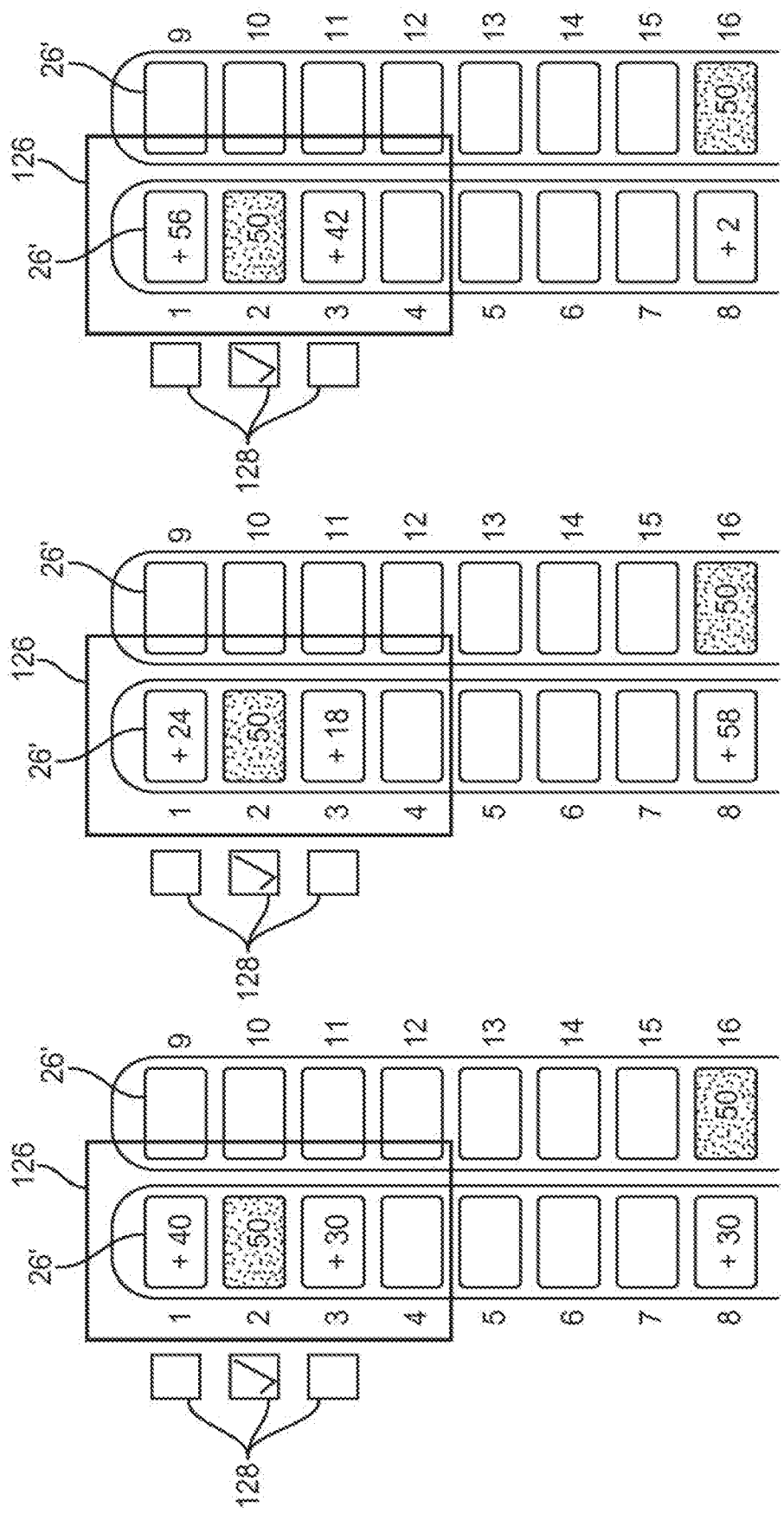

TECHNIQUE FOR LINKING ELECTRODES TOGETHER DURING PROGRAMMING OF NEUROSTIMULATION SYSTEM

RELATED APPLICATION DATA

The present application is a continuation of U.S. application Ser. No. 15/361,259, filed Nov. 25, 2016, which is a continuation of U.S. application Ser. No. 13/679,551, filed Nov. 16, 2012, now issued as U.S. Pat. No. 9,504,838, which claims the benefit under 35 U.S.C. § 119 to U.S. provisional patent application Ser. No. 61/561,760, filed Nov. 18, 2011. Each of the foregoing applications is hereby incorporated by reference into the present application in its entirety.

FIELD OF THE INVENTION

The present inventions relate to tissue stimulation systems, and more particularly, to neurostimulation systems for programming neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) and Peripheral Nerve Field Stimulation (PNFS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets. The computerized programming system may be operated by a clinician attending the patient in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy.

When electrical leads are implanted within the patient, the computerized programming system, in the context of an operating room (OR) mapping procedure, may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the painful site. Thus, the navigation session may be used to pinpoint the stimulation region or areas correlating to the pain. Such programming ability is particularly advantageous for targeting the tissue during implantation, or after implantation should the leads gradually or unexpectedly move that would otherwise relocate the stimulation energy away from the target site, or if the pain pattern has worsened or otherwise changed. By reprogramming the neurostimulator (typically by independently varying the stimulation energy on the electrodes), the stimulation region can often be moved back to the effective pain site without having to re-operate on the patient in order to reposition the lead and its electrode array. When adjusting the stimulation region relative to the tissue, it is desirable to make small changes in the proportions of current, so that changes in the spatial recruitment of nerve fibers will be perceived by the patient as being smooth and continuous and to have incremental targeting capability.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

Prior to creating the stimulation programs, the Bionic Navigator® may be operated by a clinician in a "manual programming mode" to manually select the percentage cathodic current and percentage anodic current flowing through the electrodes, or may be operated by the clinician in an "automated programming mode" to electrically "steer" the current along the implanted leads in real-time (e.g., using a joystick or joystick-like controls), thereby allowing the clinician to determine the most efficacious stimulation parameter sets that can then be stored and eventually combined into stimulation programs. Oftentimes, the Bionic Navigator® is operated in the manual programming mode to find a good starting electrode combination for the automated programming mode.

Certain computerized programming systems, such as the Bionic Navigator®, are capable of individually and independently varying the amount of current on each of the electrodes. For example, when programming the neurostimulator in a manual mode, the user may specify the polarity and percentage of current that flows through any given electrode, as described in U.S. Provisional Patent Application Ser. No. 61/486,141, entitled "Neurostimulation System With On-Effector Programmer Control," which is expressly incorporated herein by reference. While this feature provides maximum flexibility when determining the combination of electrodes required to achieve optimum therapy, modifying the specified amount of current for any given electrode will necessarily modify the amount of current previously specified for other electrodes of the same polarization, since the total current on the electrodes for the same polarization must always equal 100 percent.

Despite the seemingly unavoidable consequence of changing the already programmed current on other electrodes while specifying the current on another electrode, oftentimes, there are situations where it is desirable to maintain a certain electrode combination while adjusting the current on other electrodes. For example, in the case where there are multiple target stimulation sites corresponding to, e.g., different pain regions, it may be desirable to prevent the current values optimally programmed for a particular electrode combination covering one of the stimulation sites from changing when programming another combination of electrodes covering another stimulation site.

Because the perfect electrode combination is needed to provide optimum therapy when programming a neurostimulator in a manual mode, or to even serve as a good starting point for programming a neurostimulator in an automated mode, there thus remains a need to maintain the current values programmed for any electrode combination when programming other electrodes.

SUMMARY OF THE INVENTION

In accordance with the present inventions, an external control device is provided. The external control device can be used with a neurostimulator coupled to a plurality of electrodes capable of conveying electrical stimulation energy into tissue in which the electrodes are implanted.

The external control device comprises a user interface including at least one control element, and a processor configured for independently assigning stimulation amplitude values (e.g., fractionalized electrical current values) to a first set of the electrodes. In one embodiment, the user interface includes at least another one control element, and the processor is configured for independently assigning the stimulation amplitude values to the first set of electrodes in response to actuation of the other control element(s). In another embodiment, the processor may be further configured for designating at least one electrode of the first set of electrodes as a cathode and at least another one electrode of the first set of electrodes as an anode. The external control device further comprises output circuitry configured for transmitting the stimulation amplitude values to the neurostimulator. The external control device may further comprise a housing containing the user interface, processor, and output circuitry.

The processor is further configured for linking the first set of electrodes together in response to the actuation of the control element(s), and for preventing the stimulation amplitude values of the first linked set of electrodes from being varied relative to each other. The user interface may further include a display screen configured for displaying graphical representations of the electrodes and for graphically displaying the control elements adjacent the graphical electrode representations. In one embodiment, the control elements are symbols that can be checked, in which case, the processor is configured for linking the electrodes associated with the checked symbols. In another embodiment, the control elements are the graphical electrode representations that can be highlighted, in which case, the processor is configured for linking the electrodes associated with the highlighted electrode representations.

In one embodiment, the processor is configured for locking the first linked set of electrodes, such that fractionalized electrical current values of the first linked set of electrodes are prevented from being varied when fractionalized electrical current values of a second set of electrodes are varied. In this case, the processor may be configured for independently varying the fractionalized electrical current values of the second set of electrodes, such that an amount of fractionalized electrical current by which at least one electrode of the second set of electrodes is varied is completely compensated for in at least another one electrode of the second set of electrodes to conserve one hundred percent of the total electrical current.

In another embodiment, the processor is configured for globally scaling the stimulation amplitude values of the first linked set of electrodes. In this case, the processor may be configured for varying fractionalized electrical current values of the second set of electrodes in response to globally scaling fractionalized electrical current values of the first linked set of electrodes, such that an amount of fractionalized electrical current by which first set of electrodes is globally scaled is completely compensated for in the second set of electrodes to conserve one hundred percent of the total electrical current. The processor may optionally be configured for locking a subset of the first set of electrodes, such that the fractionalized electrical current values of the subset of electrodes are prevented from being varied when stimulation amplitude values of the first set of electrodes are globally scaled.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 11a-11c are plan views respectively illustrating one method used by the CP of FIG. 6 to globally scale a set of adjacent electrodes and independently lock a subset of the adjacent electrodes.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neurostimulator configured to treat urinary incontinence, sleep apnea, shoulder sublaxation, headache, etc.

Figure 1:
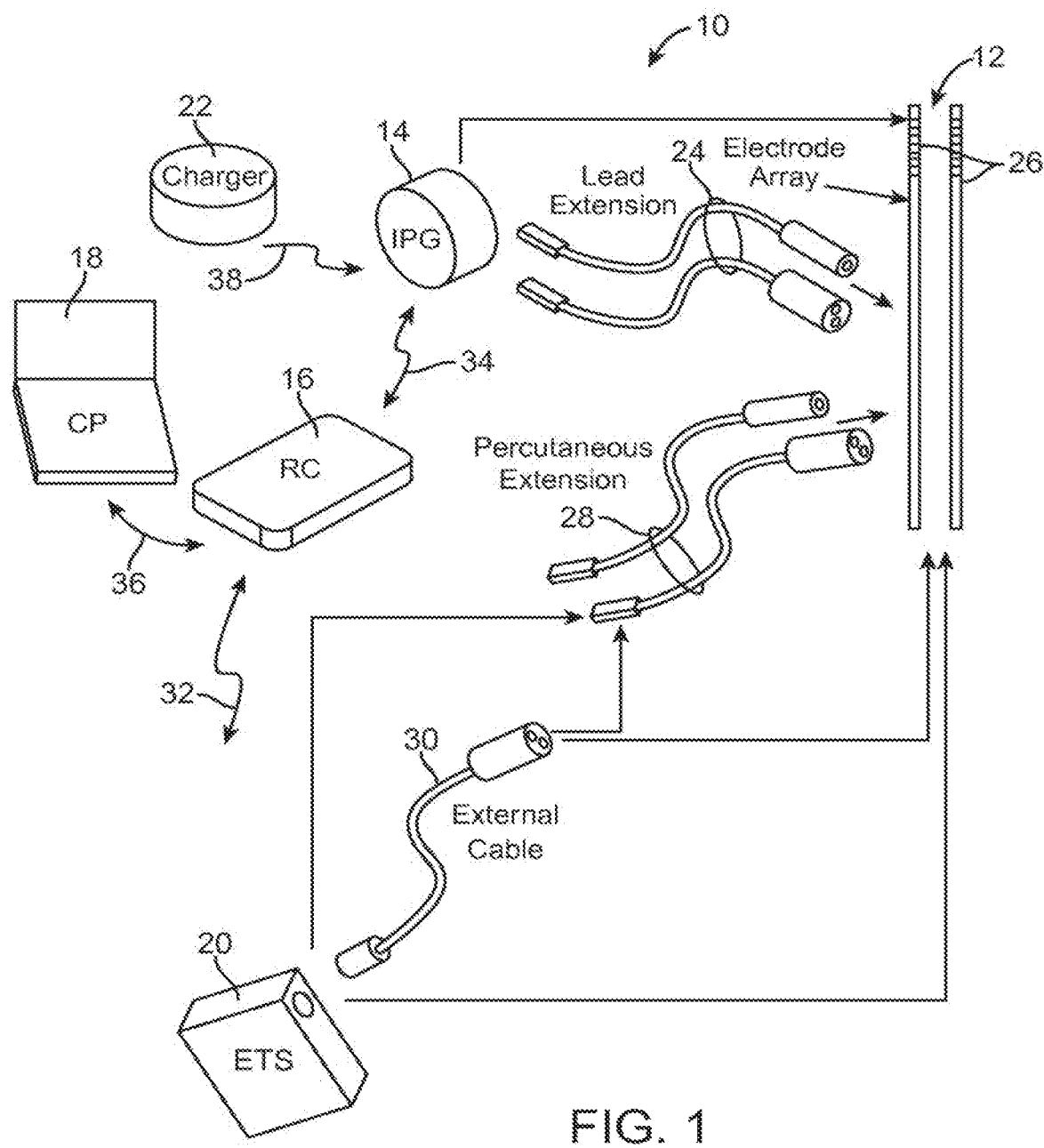
FIG. 1 is a plan view of a Spinal cord Stimulation (SCS) system constructed in accordance with one embodiment of the present inventions.

Turning first to FIG. 1, an exemplary SCS system 10 generally includes a plurality (in this case, two) of implantable neurostimulation leads 12, an implantable pulse generator (IPG) 14, an external remote controller RC 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. Alternatively, a surgical paddle lead may be used in place of or in addition to the percutaneous leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
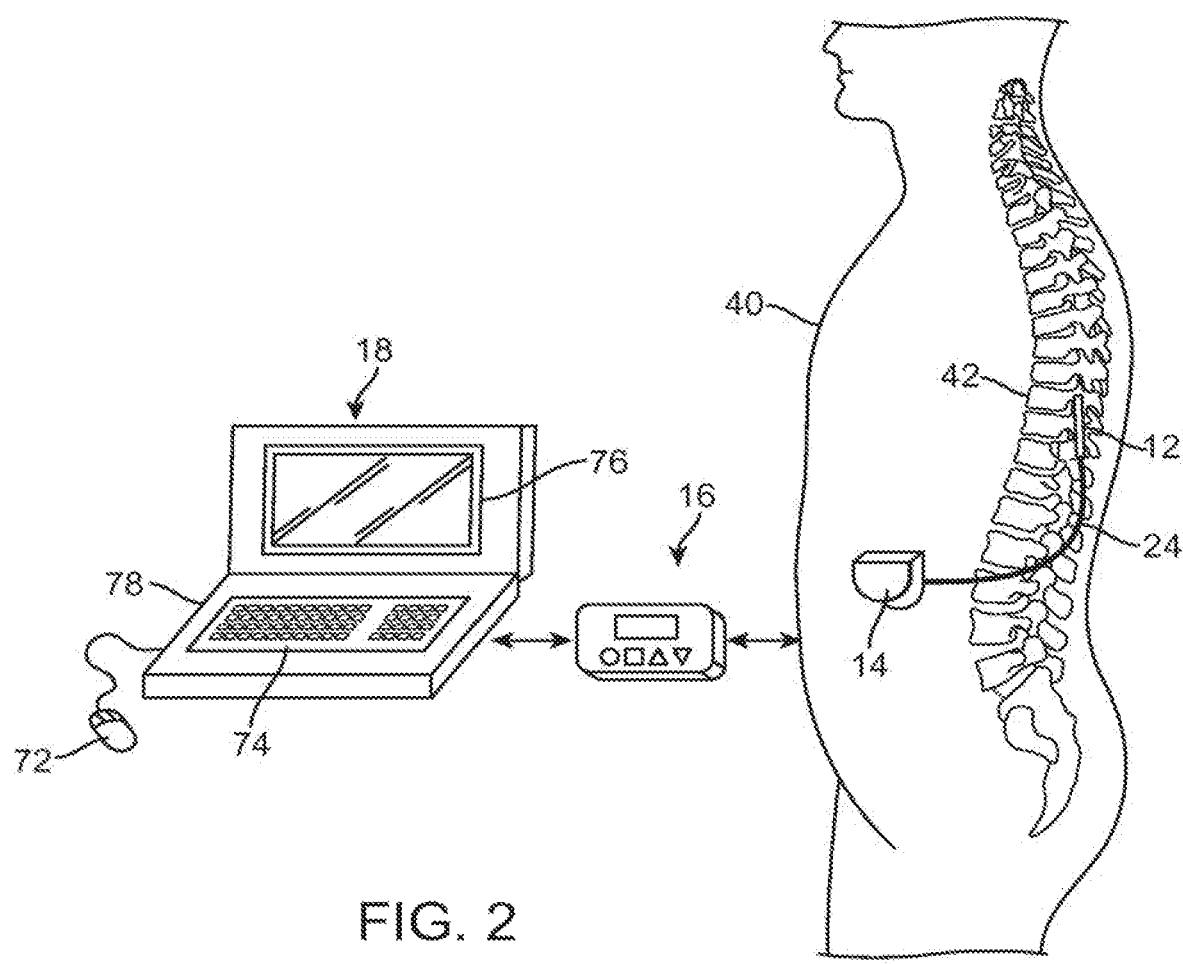
FIG. 2 is a perspective view of the arrangement of the SCS system of FIG. 1 with respect to a patient.

As shown in FIG. 2, the electrode leads 12 are implanted within the spinal column 42 of a patient 40. The preferred placement of the electrode leads 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
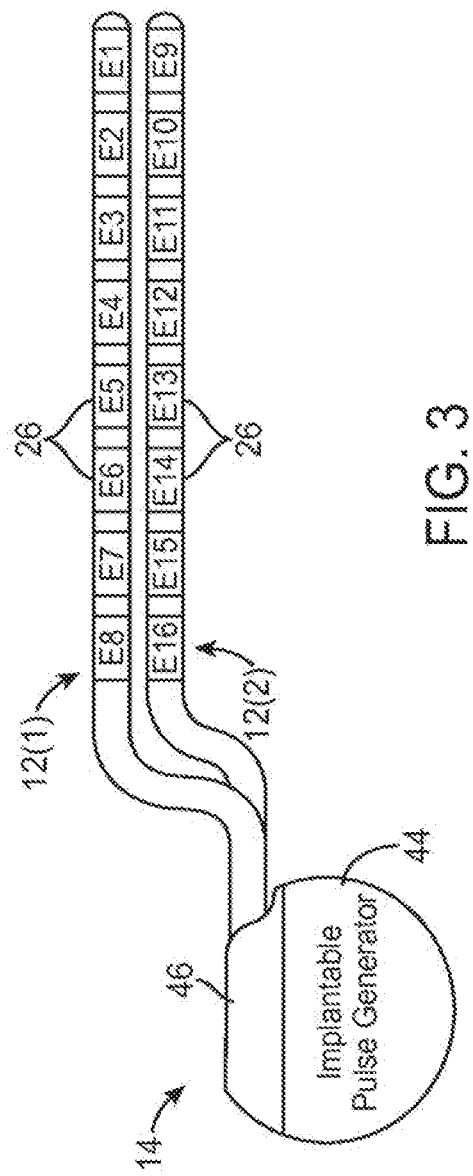
FIG. 3 is a profile view of an implantable pulse generator (PG) and percutaneous leads used in the SCS system of FIG. 1.

Referring now to FIG. 3, the external features of the neurostimulation leads 12 and the IPG 14 will be briefly described. One of the neurostimulation leads 12(1) has eight electrodes 26 (labeled E1-E8), and the other neurostimulation lead 12(2) has eight electrodes 26 (labeled E9-E16). The actual number and shape of leads and electrodes will, of course, vary according to the intended application. The IPG 14 comprises an outer housing 40 for housing the electronic and other components (described in further detail below), and a connector 42 to which the proximal ends of the neurostimulation leads 12 mates in a manner that electrically couples the electrodes 26 to the electronics within the outer housing 40. The outer housing 40 is composed of an electrically conductive, biocompatible material, such as titanium, and forms a hermetically sealed compartment wherein the internal electronics are protected from the body tissue and fluids. In some cases, the outer housing 40 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode combinations and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc. fashion. Monopolar stimulation occurs when a selected one of the lead electrodes 26 is activated along with the housing 40 of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
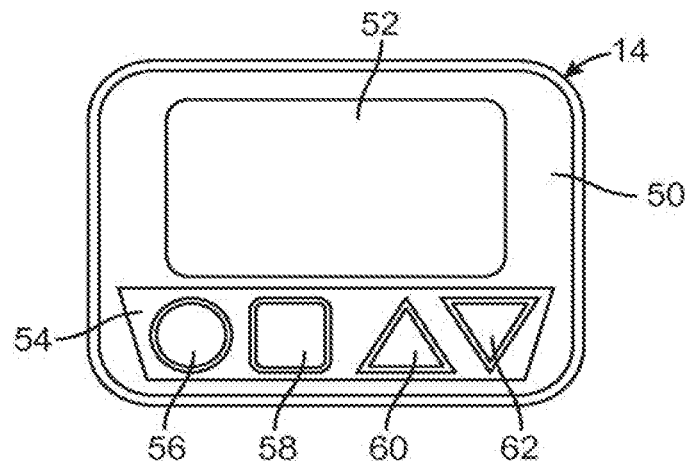
FIG. 4 is front view of a remote control (RC) used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a housing 50, which houses internal componentry (including a printed circuit board (PCB)), and a lighted display screen 52 and button pad 54 carried by the exterior of the housing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touch screen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
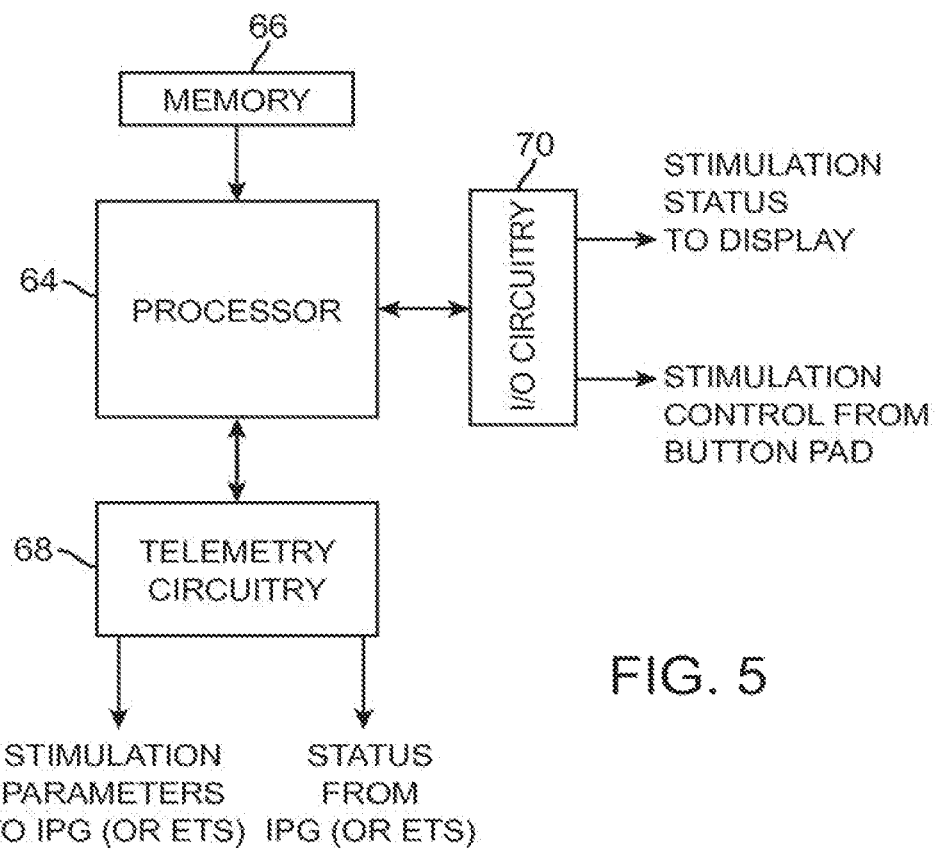
FIG. 5 is a block diagram of the internal components of the RC of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a navigation table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

Figure 6:
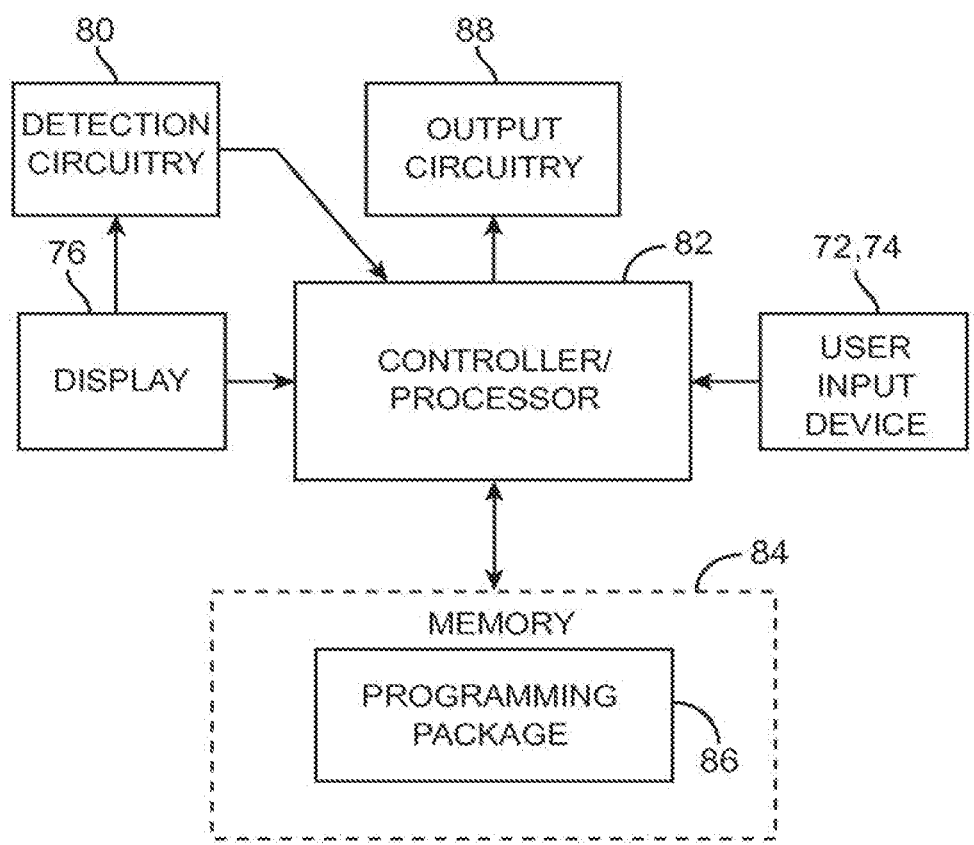
FIG. 6 is a block diagram of the internal components of a clinician's programmer (CP) used in the SCS system of FIG. 1.

To allow the user to perform these functions, the CP 18 includes a mouse 72, a keyboard 74, and a programming display screen 76 housed in a housing 78. It is to be understood that in addition to, or in lieu of, the mouse 72, other directional programming devices may be used, such as a joystick, a button pad, a group of keyboard arrow keys, a roller ball tracking device, and horizontal and vertical rocker-type arm switches. Referring to FIG. 6, the CP 18 further includes detection circuitry 80 capable of detecting an actuation event on the display screen 76. Such actuation event may include placing at least one pointing element (not shown) in proximity to at least one graphical object displayed on the display screen 76, as well as possibly other events involving the point element(s), such as moving the pointing element(s) across the screen or clicking or tapping with the pointing element(s), as will be described in further detail below.

In the preferred embodiments described below, the display screen 76 takes the form of a digitizer touch screen, which may either passive or active. If passive, the detection circuitry 80 recognizes pressure or a change in an electrical current when a passive device, such as a finger or non-electronic stylus, contacts the screen. If active, the detection circuitry 80 recognizes a signal transmitted by an electronic pen or stylus. In either case, the detection circuitry 80 is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. In some embodiments, the display screen 76 takes the form of a conventional screen, in which case, the pointing element is not an actual pointing device like a finger or stylus, but rather is a virtual pointing device, such as a cursor controlled by a mouse, joy stick, trackball, etc.

As shown in FIG. 6, the CP 18 generally includes a controller/processor 82 (e.g., a central processor unit (CPU)) and memory 84 that stores a stimulation programming package 86, which can be executed by the controller/controller/processor 82 to allow the user to program the IPG 14, and RC 16. The CP 18 further includes output circuitry 88 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16. Notably, while the controller/processor 82 is shown as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by a processor.

Execution of the programming package 86 by the controller/processor 82 provides a multitude of display screens (not shown) that can be navigated through via use of afore-described pointing device. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, now issued as U.S. Pat. No. 9,278,222, entitled "System and Method for Converting Tissue Stimulation Programs in a Format Usable by an Electrical Current Steering Navigator," and U.S. patent application Ser. No. 12/614,942, published as US 2010/0121409 A1, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 86 provides a user interface that allows a user to link selected electrodes 26 together during programming of the IPG 14, such that stimulation amplitude values, and in this case fractionalized current values previously assigned to these electrodes 26, cannot be varied relative to each other. For example, these electrodes 26 can be locked such that their fractionalized electrical current values are prevented from being varied when the fractionalized electrical current values of other electrodes 26 are varied. As another example, these electrodes 26 can be linked, such that their stimulation amplitudes values can be globally scaled up or down.

Figure 7:
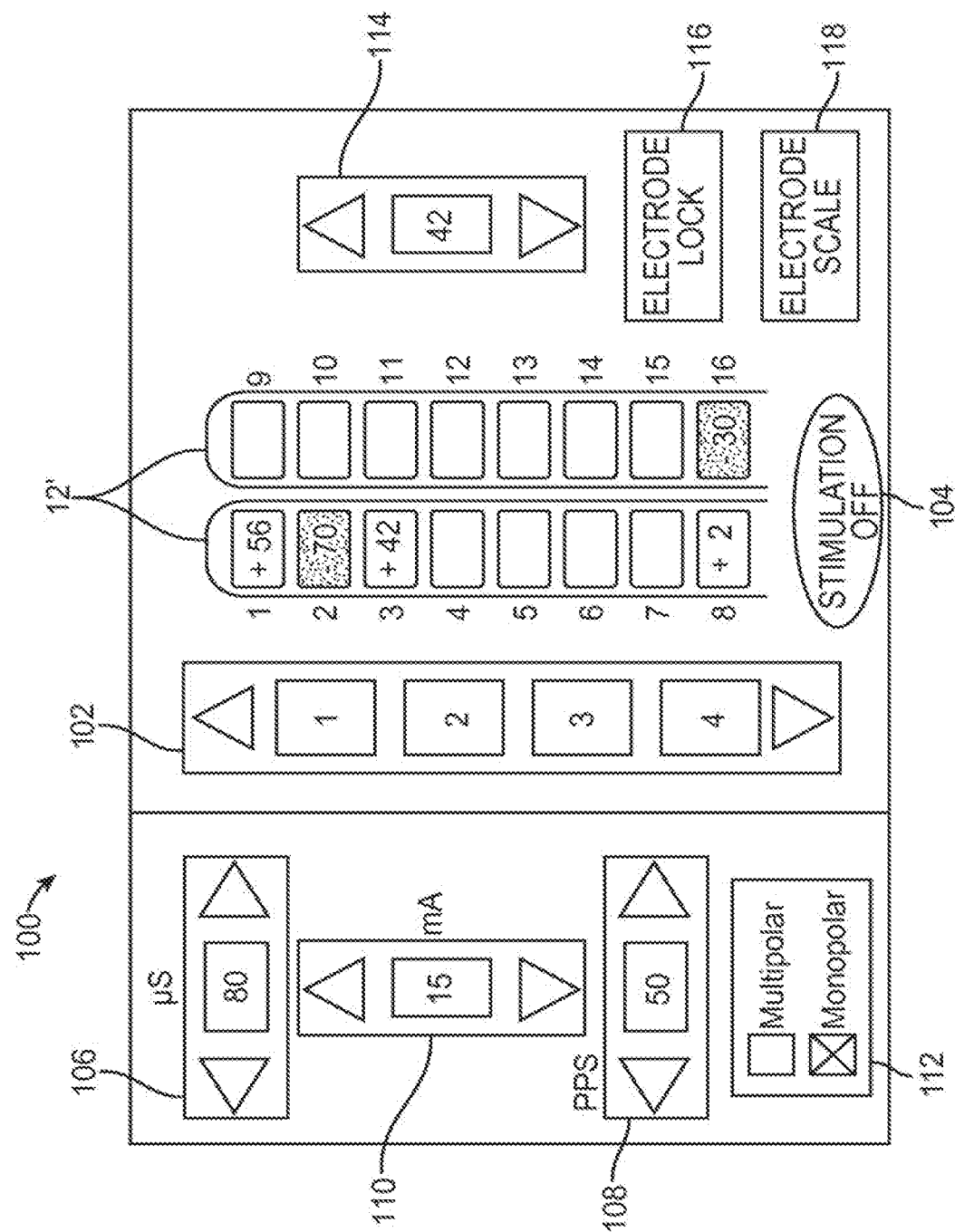
FIG. 7 is a plan view of a user interface of the CP of FIG. 6 for programming the IPG of FIG. 3.

Referring now to FIG. 7, an exemplary programming screen 100 generated by the CP 16 to allow a user to program the IPG 14 will now be described. The programming screen 100 includes various control elements described below that can be actuated to perform various control functions.

A pointing element may be placed on any of the control elements to perform the actuation event. As described above, in the case of a digitizer touch screen, the pointing element will be an actual pointing element (e.g., a finger or active or passive stylus) that can be used to physically tap the screen above the respective graphical control element or otherwise brought into proximity with respect to the graphical control element. In the case of a conventional screen, the pointing element will be a virtual pointing element (e.g., a cursor) that can be used to graphically click on the respective control element.

The programming screen 100 includes an electrode combination control 102 having arrows that can be actuated by the user to select one of four different electrode combinations 1-4. The programming screen 100 further includes a stimulation on/off control 104 that can be alternately actuated initiate or cease the delivery of electrical stimulation energy from the IPG 14 via the selected electrode combination.

The programming screen 100 further includes various stimulation parameter controls that can be operated by the user to manually adjust stimulation parameters for the selected electrode combination. In particular, the programming screen 100 includes a pulse width adjustment control 106 (expressed in microseconds (μs)), a pulse rate adjustment control 108 (expressed in Hertz (Hz)), and a pulse amplitude adjustment control 110 (expressed in milliamperes (mA)). Each control includes a first arrow that can be actuated to decrease the value of the respective stimulation parameter and a second arrow that can be actuated to increase the value of the respective stimulation parameter.

Each of the electrode combinations 1-4 can be created using various control elements. In particular, the programming screen 100 displays graphical representations of the leads 12' including the electrodes 26'. In the illustrated embodiment, each electrode representation 26' takes the form of a closed geometric figure, and in this case a rectangle. In alternative embodiments, the electrode representations 26' can take the form of other types of closed geometric figures, such as circles. The electrode representations 26' can be touched with a physical pointing device or otherwise clicked with a virtual pointing device multiple times to switch the corresponding active electrode 26 between a positive polarity (anode), a negative polarity cathode), and an off-state. In essence, the electrode representations 26' themselves operate as the graphical control elements, the actuations of which prompt the controller/processor 82 to assign the polarities to the selected electrodes 26. In alternative embodiments, control elements separate from the electrode representations 26' may be used to change the polarity of the selected electrodes 26.

To enable selection between a multipolar configuration and a monopolar configuration, the programming screen 100 also includes multipolar/monopolar stimulation selection control 112, which includes check boxes that can be alternately actuated by the user to selectively provide multipolar or monopolar stimulation. If a multipolar electrode arrangement is desired, at least one of the electrodes E1-E16 will be selected as an anode (+) and at least one other of the electrodes E1-E16 will be selected as a cathode (−). If a monopolar electrode arrangement is desired, none of the electrodes E1-E16 will be selected as an anode (+), and thus, the electrode presentations 26' can only be clicked to toggle the corresponding electrode 26 between a cathode (−) and off (0).

The programming screen 100 further includes an electrode specific current adjustment control 114 that can be manipulated to independently vary stimulation amplitude values for the electrodes E1-E16. In particular, for each electrode selected to be activated as either a cathode or anode, the clinician can click on the upper arrow of the control 114 to incrementally increase the absolute value of the stimulation amplitude of the selected electrode, and the clinician can click on the lower arrow of the control 114 to incrementally decrease the absolute value of the stimulation amplitude of the selected electrode. The control 114 also includes an indicator that provides an alphanumeric indication of the stimulation amplitude currently assigned to the selected electrode. In an optional embodiment, non-alphanumeric indicators, such as different colors, different color luminances, different patterns, different textures, different partially-filled objects, etc., can be used to indicate the stimulation amplitude currently assigned to the selected electrodes, as discussed in U.S. patent application Ser. No. 13/200,629, published as US 2012/0109230 A1, entitled "Neurostimulation System and Method for Graphically Displaying Electrode Stimulation Values," which is expressly incorporated herein by reference.

In the illustrated embodiments, the stimulation amplitude values are fractionalized electrical current values (% current), such that the values for each polarization totals to 100. However, in alternative embodiments, the stimulation amplitude values may be normalized current or voltage values (e.g., 1-10), absolute current or voltage values (e.g., mA or V), etc. Furthermore, the stimulation amplitude values may be parameters that are a function of current or voltage, such as charge (current amplitude×pulse width) or charge injected per second (current amplitude×pulse width× rate (or period)).

In alternative embodiments, a stimulation amplitude adjustment control (not shown) may appear next to the electrode representation 26' that has been touched or clicked, as described in U.S. patent application Ser. No. 13/200,629, published as US 2012/0109230 A1, which has been previously incorporated herein by reference, or may be superimposed over the electrode representation 26' that has been touched or clicked, as described in U.S. Provisional Patent Application Ser. No. 61/486,141, entitled "Neurostimulation System with On-Effector Programmer Control," which is expressly incorporated herein by reference.

In alternative embodiments, the programming screen 100 facilitates automated current steering; for example, by allowing the user to switch between a manual mode using the electrode selection and current adjustment techniques described above, an electronic trolling ("e-troll") mode that quickly sweeps the electrode array using a limited number of electrode configurations to gradually move a cathode in bipolar stimulation, and a Navigation programming mode that finely tunes and optimizes stimulation coverage for patient comfort using a wide number of electrode configurations, as described in U.S. Provisional Patent Application Ser. No. 61/576,924, entitled "Seamless Integration of Different Programming Modes for a Neurostimulator Programming System," which is expressly incorporated herein by reference. Virtual target poles may be utilized to steer the current within the electrode array, as described in U.S. Provisional Patent Application Ser. No. 61/452,965, entitled "Neurostimulation System for Defining a Generalized Virtual Multipole," which is expressly incorporated herein by reference.

As briefly discussed above, selected ones of the electrodes 26 can be linked together, such that the fractionalized electrical current values previously assigned to them via manipulation of the current adjustment control 114 cannot be varied relative to each other. In the illustrated embodiment, the programming screen 100 includes an electrode locking control 116 that can be actuated (e.g., touched or clicked) to allow selected electrodes 26 to be locked, thereby preventing the fractionalized electrical values previously assigned to the selected electrodes from being subsequently varied. The programming screen 100 also includes a global electrode scaling control 118 that can be actuated (e.g., touched or clicked) to allow the fractionalized electrical values previously assigned to the selected electrodes 26 to be globally scaled.

In one embodiment, the actuation of the electrode locking control 116 prompts the controller/processor 82 to display graphical control symbols, such as boxes, respectively adjacent the electrode representations 26'. These symbols can then be checked to prompt the controller/processor 82 to link together, and in this case to lock, a first set of electrodes 26 corresponding to these checked symbols, such that fractionalized electrical current values initially assigned to these electrodes are prevented from being varied when fractionalized electrical current values of a second set of electrodes are varied. In alternative embodiments, the graphical symbols can take the form of closed geometric figures other than boxes, such as circles, stars, triangles, etc. With reference now to FIGS. 8a-8e, one example of using check boxes 120 to lock selected electrodes will be discussed.

Figure 8C:
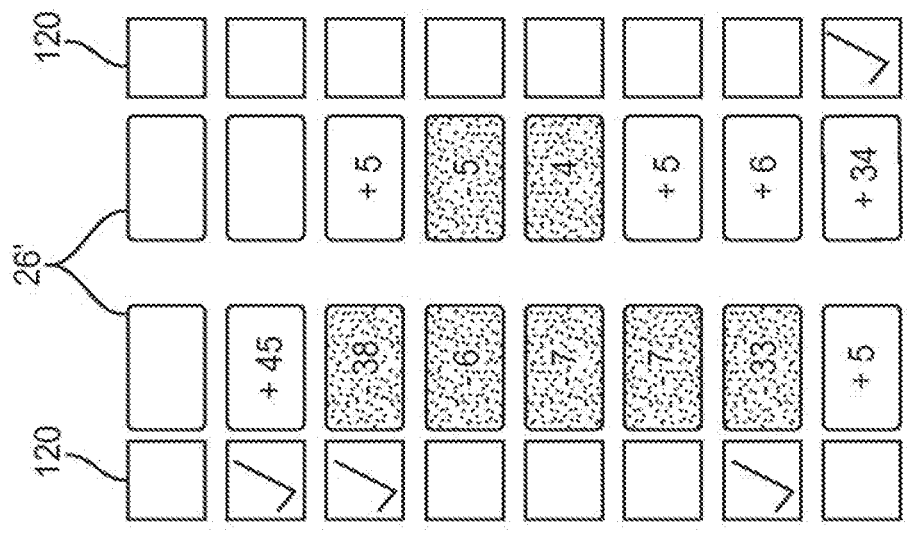
FIGS. 8a-8c are plan views respectively illustrating one method used by the CP of FIG. 6 to independently lock selected electrodes.
Figure 8B:
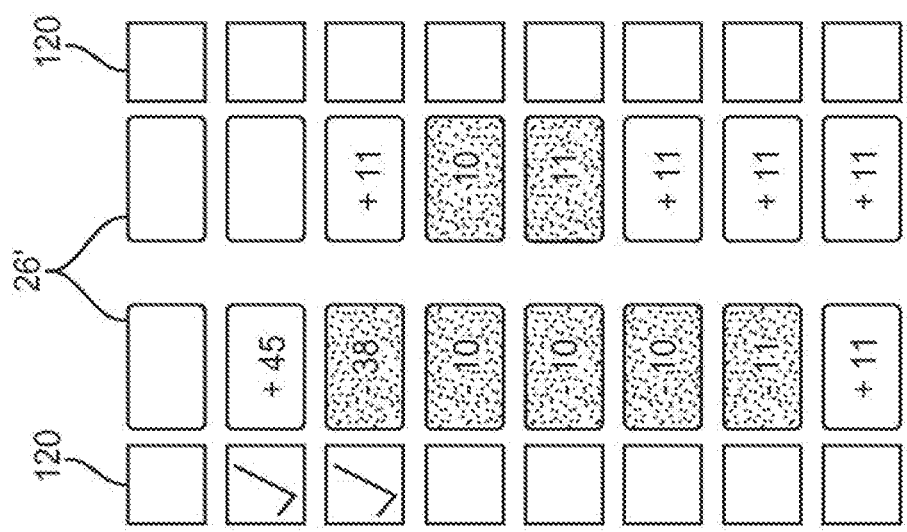
Figure 8A:
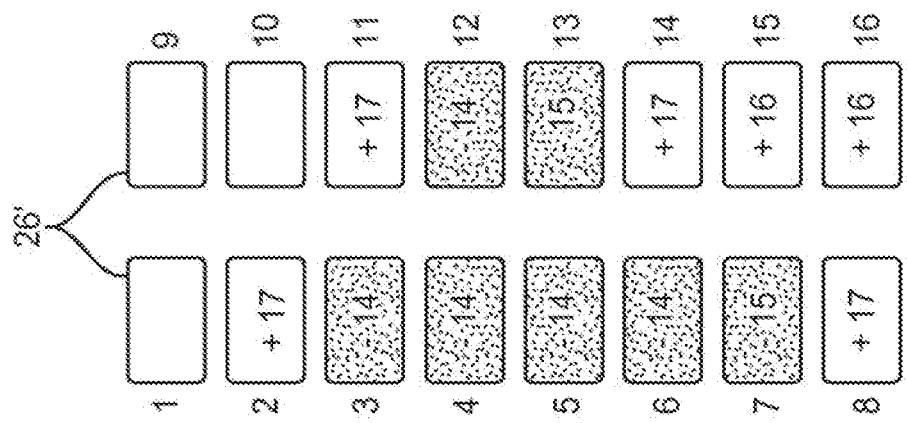

As illustrated in FIG. 8a, electrodes E2, E8, E11, and E14-E16 have been initially assigned equalized fractionalized anodic current values, and electrodes E3-E7 and E12-E13 have been initially assigned equalized fractionized cathodic current values.

As illustrated in FIG. 8b, the current adjustment control 114 has been actuated at separate times to independently increase the fractionalized anodic current for electrode E2 to 45% and to increase the fractionalized cathodic current for electrode E3 to 38%. The amount of fractionalized current by which electrodes E2-E3 is varied is completely compensated for in the remaining active electrodes to conserve 100% of the total electrical current. In particular, the fractionalized anodic current for electrode E2 has been changed by 28% (from 17% to 45%), which is compensated for by decreasing the fractionalized anodic current for each of electrodes E8, E11, and E14-16 by 5% or 6%, and the fractionalized cathodic current for electrode E3 has been changed by 24% (from 14% to 38%), which is compensated for by decreasing the fractionalized cathodic current for each of electrodes E4-E7 and E12-E13 by 4%.

Furthermore, the electrode locking control 116 (shown in FIG. 7) has been actuated to display the check boxes 120 adjacent all the electrode representations 26', with the check boxes 120 adjacent the electrode representations associated with electrodes E2-E3 being checked, indicating that electrodes E2-E3 have been locked, such that the respective fractionalized cathodic and anodic current values of 45% and 38% are not varied when the fractionalized current values on the remaining unlocked active electrodes are varied, unlocked active electrodes are deactivated, and/or previously inactive electrodes are activated.

For example, as shown in FIG. 8c, the current adjustment control 114 (shown in FIG. 7) has been actuated at separate times to independently increase the fractionalized cathodic current for electrode E7 to 33% and to increase the fractionalized anodic current for electrode E16 to 34%. While maintaining the fractionalized anodic current for electrode E2 at 45% and the fractionalized cathodic current for electrode E3 at 38%, the amount of fractionalized current by which electrodes E7 and E16 is varied is completely compensated for in the remaining active electrodes to conserve 100% of the total electrical current. In particular, the fractionalized cathodic current for electrode E7 has been changed by 22% (from 11% to 33%), which is compensated for by decreasing the fractionalized cathodic current for each of electrodes E4-E6 and E12-E13 by 4% or 5%, and the fractionalized anodic current for electrode E16 has been changed by 23% (from 11% to 34%), which is compensated for by decreasing the fractionalized anodic current for each of electrodes E8, E11, and E14-E15 by 6%.

Furthermore, the check boxes 120 adjacent the electrode representations associated with electrodes E7 and E16 are shown as being checked, indicating that electrodes E7 and E16 (in addition to electrodes E2 and E3) have been locked, such that the respective fractionalized cathodic and anodic current values of 33% and 34% are not varied when the fractionalized current values on the remaining unlocked active electrodes are varied, unlocked active electrodes are deactivated, and/or previously inactive electrodes are activated. Notably, any of the previously checked boxes 120 may be touched or otherwise clicked again to uncheck the check boxes 120, thereby unlocking the electrodes associated with the electrode representations 26' adjacent the unchecked boxes 120, such that fractionalized electrical current values assigned to these electrodes can again be varied.

Figure 9C:
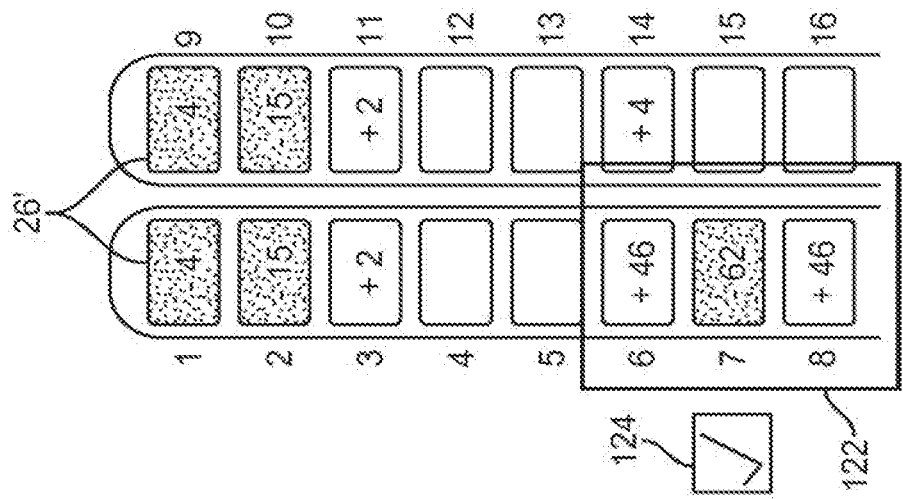
FIGS. 9a-9c are plan views respectively illustrating one method used by the CP of FIG. 6 to lock a set of adjacent electrodes.
Figure 9B:
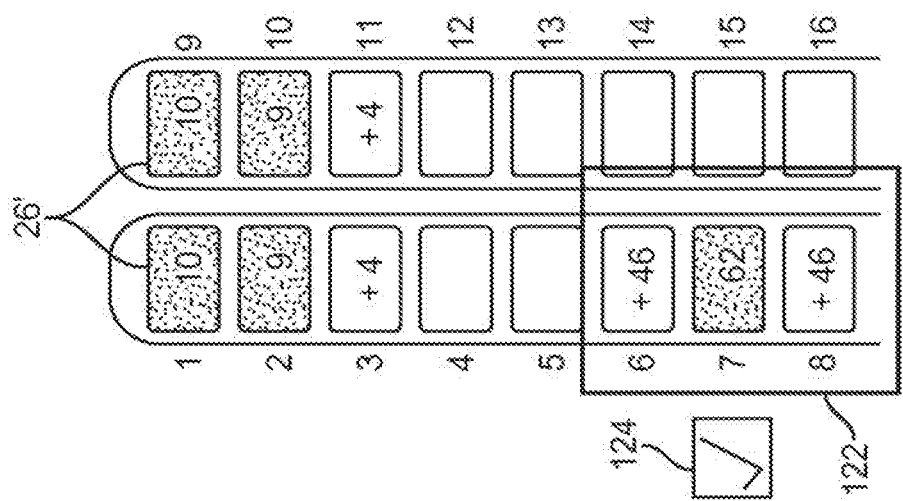
Figure 9A:
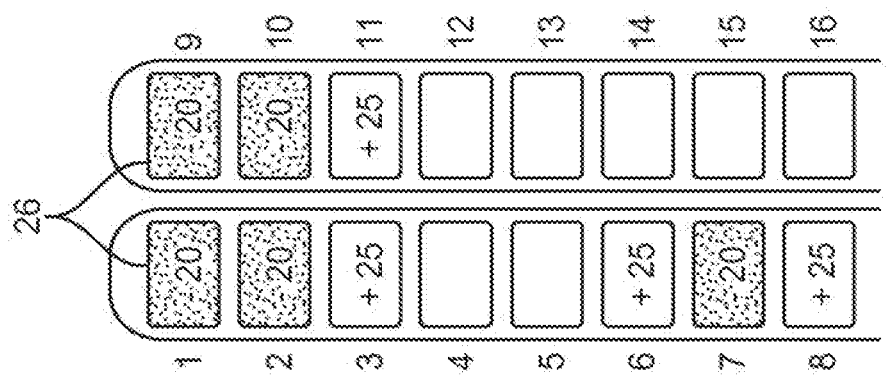

In an alternative embodiment, rather than using control elements in the form of check boxes to lock electrodes, the actuation of the electrode locking control 116 prompts the controller/processor 82 to enable a group of adjacent electrode representations 26' to be highlighted to lock a first set of electrodes 26 corresponding to the highlighted electrode representations 26', such that fractionalized electrical current values initially assigned to these electrodes are prevented from being varied when fractionalized electrical current values of a second set of electrodes are varied. With reference now to FIGS. 9a-9c, one example of highlighting electrode representations 26' to lock selected electrodes will be discussed.

As illustrated in FIG. 9a, electrodes E1-E2, E7, and E9-E10 have been initially assigned equalized fractionalized cathodic current values, and electrodes E3, E6, E8, and E11 have been initially assigned equalized fractionized anodic current values.

As illustrated in FIG. 9b, the current adjustment control 114 has been actuated at separate times to independently increase the fractionalized cathodic current for electrode E7 to 62% and to increase the fractionalized anodic current for each of electrode E6 and E8 to 46%. The amount of fractionalized current by which electrodes E6-E8 is varied is completely compensated for in the remaining active electrodes to conserve 100% of the total electrical current. In particular, the fractionalized cathodic current for electrode E7 has been changed by 42% (from 20% to 62%), which is compensated for by decreasing the fractionalized cathodic current for each of electrodes E1-E2 and E9-E10 by 10% or 11%, and the fractionalized anodic current for electrodes E6 and E8 in total has been changed by 42% (from 50% to 92%), which is compensated for by decreasing the fractionalized anodic current for each of electrodes E3 and E11 by 21%.

Furthermore, the group of adjacent electrodes E6-E8 are highlighted with a box 122, which can be accomplished, e.g., by dragging an actual or virtual pointing device across the screen to create the box 122. A single check box 124 with a check is also displayed adjacent the box 122, indicating that electrodes E6-E8 have been locked, such that the respective fractionalized anodic, cathodic, and anodic current values of 46%, 62%, and 46% are not varied when the fractionalized current values on the remaining unlocked active electrodes are varied, unlocked active electrodes are deactivated, and/or previously inactive electrodes are activated. The previously checked box 122 may be touched or otherwise clicked again to uncheck the box 124, thereby unlinking the electrodes associated with the electrode representations 26' previously highlighted by the box 122, such that fractionalized electrical current values for these electrodes can again be independently varied relative to each other.

As shown in FIG. 9c, the current adjustment control 114 has been actuated at separate times to independently increase the fractionalized cathodic current for each of electrodes E2 and E10 to 15%. Furthermore, the electrode representation corresponding to electrode E14 has been actuated to designate the electrode E14 as an anode, and the current adjustment control 114 has been actuated to initially assign a fractionalized anodic current for electrodes E14 to 4%. While maintaining the fractionalized anodic current for electrode E6 at 46%, fractionalized cathodic current for electrode E7 at 62%, and the fractionalized anodic current for electrode E8 at 46%, the amount of fractionalized current by which electrodes E2, E10, E14 is varied is completely compensated for in the remaining active electrodes to conserve 100% of the total electrical current. In particular, the fractionalized cathodic current for electrodes E2 and E10 has been changed by a total of 12% (from 18% to 30%), which is compensated for by decreasing the fractionalized cathodic current for each of electrodes E1 and E9 by 6%, and the fractionalized anodic current for electrode E14 has been changed by 4% (from 0% to 4%), which is compensated for by decreasing the fractionalized anodic current for each of electrodes E3 and E11 by 2%.

Referring back to FIG. 7, in one embodiment, actuation of the global electrode scaling control 118, like the actuation of the electrode locking control 116, prompts the controller/processor 82 to enable a group of adjacent electrode representations 26' to be highlighted in order to link the electrodes 26 corresponding to the highlighted electrode representations 26'. However, in this case, highlighting a set of electrodes does not lock them to prevent varying the fractionalized electrical current values initially assigned to these electrodes in an absolute sense as with the electrode locking control 116. Rather, highlighting these electrodes allows the fractionalized electrical current values of the linked electrodes to be globally scaled (in effect, the fractionalized electrical current values cannot be varied independently of each other, but can only be varied in proportion to each other). With reference now to FIGS. 10a-10e, one example of highlighting electrode representations 26' to globally scale electrodes will be discussed.

Figure 10C:
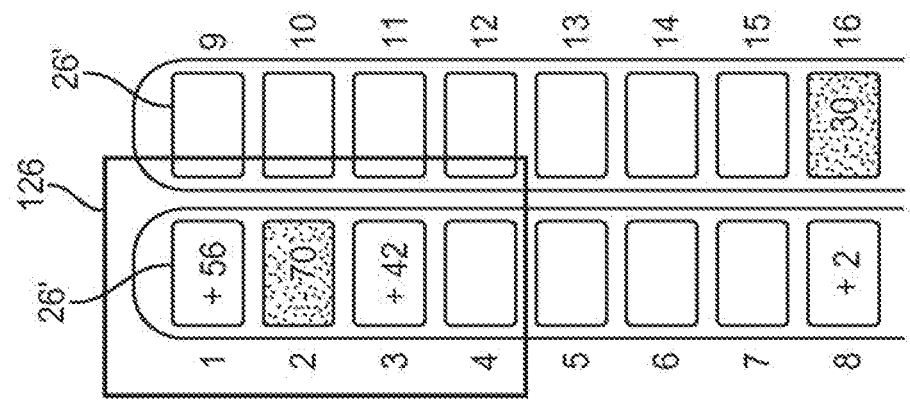
FIGS. 10a-10c are plan views respectively illustrating one method used by the CP of FIG. 6 to globally scale a set of adjacent electrodes.
Figure 10B:
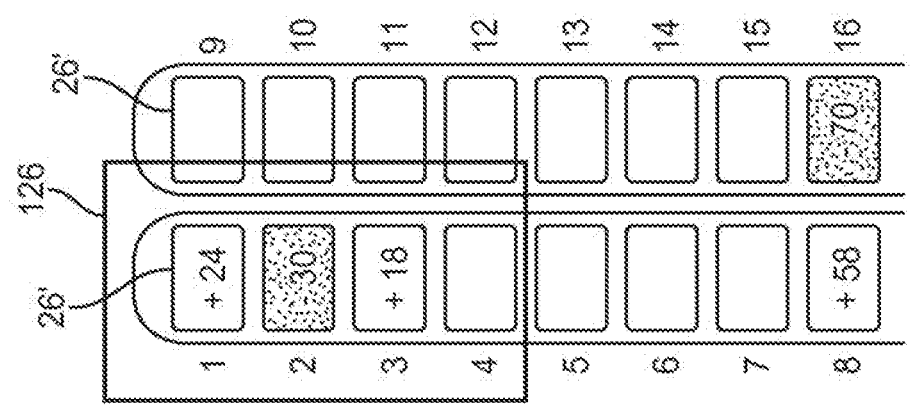
Figure 10A:
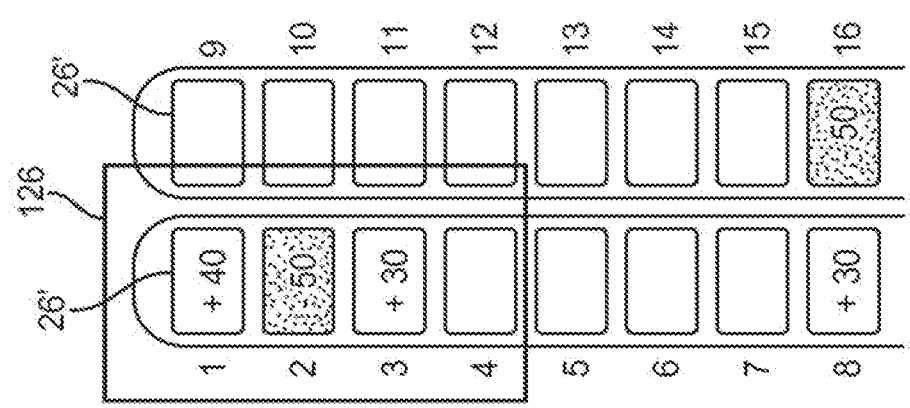

As illustrated in FIG. 10a, fractionalized anodic current values of 40%, 30%, and 30% have been initially assigned to electrodes E1, E3, and E8, respectively, and a fractionalized cathodic current value of 50% has been initially assigned to each of electrodes E2 and E16. Furthermore, the global electrode scaling control 118 has been actuated to allow the electrode representations associated with electrodes E1-E3 to be highlighted with a box 126 (e.g., by dragging an actual or virtual pointing device across the screen to create the box 126), indicating that electrodes E1-E3 have been linked, such that the respective fractionalized anodic, cathodic, and anodic current values of 40%, 50%, and 30% can be globally scaled. The previously checked box 126 may be touched or otherwise clicked again, thereby unlinking the electrodes associated with the electrode representations 26' previously highlighted by the box 126, such that fractionalized electrical current values for these electrodes can again be independently varied relative to each other.

As shown in FIG. 10b, the current adjustment control 114 can be actuated one time to globally scale the fractionalized current values for electrodes E1-E3 downward, and in this case, by globally scaling the fractionalized current values down by 40%, so that the fractionalized anodic current value for electrode E1 is decreased from 40% to 24%, the fractionalized cathodic current value for electrode E2 is decreased from 50% to 30%, and the fractionalized anodic current value for electrode E3 is decreased from 30% to 18%. As can be appreciated, the ratio of currents between electrodes E1-E3 is maintained. The amount of fractionalized current by which electrodes E1-E3 is varied is completely compensated for in the remaining active electrodes to conserve 100% of the total electrical current. In particular, the fractionalized anodic current in total for electrodes E1 and E3 has been changed by 28% (from 70% to 42%), which is compensated for by increasing the fractionalized anodic current for electrode E8 by 28% (from 30% to 58%), and the fractionalized cathodic current for electrode E2 has been changed by 20% (from 50% to 30%), which is compensated for by increasing the fractionalized cathodic current for electrode E16 by 20% (from 50% to 70%).

As shown in FIG. 10c, the current adjustment control 114 can be actuated one time to globally scale the fractionalized current values for electrodes E1-E3 upward, and in this case, by globally scaling the fractionalized current values up by 233% (relative to the state of the electrodes in FIG. 10b), so that the fractionalized anodic current value for electrode E1 is increased from 24% to 56%, the fractionalized cathodic current value for electrode E2 is increased from 30% to 70%, and the fractionalized anodic current value for electrode E3 is increased from 18% to 42%. Again, the ratio of currents between electrodes E1-E3 is maintained, and the amount of fractionalized current by which electrodes E1-E3 is varied is completely compensated for in the remaining active electrodes to conserve 100% of the total electrical current. In particular, the fractionalized anodic current in total for electrodes E1 and E3 has been changed by 56% (from 42% to 98%), which is compensated for by decreasing the fractionalized anodic current for electrode E8 by 56% (from 58% to 2%), and the fractionalized cathodic current for electrode E2 has been changed by 40% (from 30% to 70%), which is compensated for by decreasing the fractionalized cathodic current for electrode E16 by 40% (from 70% to 30%).

In an alternative embodiment, rather than highlighting a group of adjacent electrode representations 26', control elements in the form of check boxes can be displayed adjacent all the electrode representations 26' upon actuation of the global electrode scaling control 118 much like that shown in the embodiment in FIGS. 8a-8c, except that electrodes 26 corresponding to the electrode representations 26' are not locked, but rather are enabled for global scaling of their fractionalized electrical current values.

In an optional embodiment, symbols in the form of, e.g., boxes, can be respectively displayed respectively adjacent the electrode representations 26' that have been highlighted for global scaling, so that the corresponding electrodes can be selectively locked or unlocked. That is, the symbols can be checked to lock a subset of electrodes within the highlighted group of electrodes, such that fractionalized electrical current values initially assigned to this subset of electrodes are prevented from being varied when the fractionalized electrical current values for the highlighted group of electrodes are globally scaled.

With reference now to FIGS. 1a-11c, one example of highlighting electrode representations 26' to globally scale electrodes will be discussed.

The display of FIG. 11a is similar to that of FIG. 10a, with the exception that the highlighting of electrodes E1-E3 with the box 126 prompts the display of check boxes 128 adjacent the electrode representations 26' corresponding to electrodes E1-E3. The check box 126 adjacent the electrode representation associated with electrode E2 being checked, indicating that electrode E2 has been locked, such that the fractionalized cathodic current value of 50% is not varied when the fractionalized current values on the remaining unlocked electrodes in the highlighted group of electrodes E1-E3 are varied.

As shown in FIG. 11b, the current adjustment control 114 can be actuated one time to globally scale the fractionalized current values for electrodes E1 and E3 downward, and in this case, by globally scaling the fractionalized current values by 40%, so that the fractionalized anodic current value for electrode E1 is decreased from 40% to 24%, and the fractionalized anodic current value for electrode E3 is decreased from 30% to 18%, similar to that illustrated in FIG. 10b. However, in this case, the fractionalized cathodic current for electrode E2 is not varied when the fractionalized current values on electrodes E1 and E3 are globally scaled. The amount of fractionalized current by which electrodes E1 and E3 is varied is completely compensated for in the remaining active electrodes to conserve 100% of the total electrical current in the same manner discussed above with respect to FIG. 10b. Because the fractionalized cathodic current for electrode E2 is not varied, no compensation is required, and thus, the fractionalized cathodic current for electrode E16 is not varied.

As shown in FIG. 11c, the current adjustment control 114 can be actuated one time to globally scale the fractionalized current values for electrodes E1 and E3 upward, and in this case, by globally scaling the fractionalized current values by 233% (relative to the state of the electrodes in FIG. 11b), so that the fractionalized anodic current value for electrode E1 is increased from 24% to 56%, and the fractionalized anodic current value for electrode E3 is decreased from 18% to 42%. Again, in this case, the fractionalized cathodic current for electrode E2 is not varied when the fractionalized current values on electrodes E1 and E3 are globally scaled. The amount of fractionalized current by which electrodes E1 and E3 is varied is completely compensated for in the remaining active electrodes to conserve 100% of the total electrical current in the same manner discussed above with respect to FIG. 10e. Because the fractionalized cathodic current for electrode E2 is not varied, no compensation is required, and thus, the fractionalized cathodic current for electrode E16 is not varied.

Although the electrode locking techniques (FIGS. 8 and 9) and the global scaling techniques (FIGS. 10 and 11) have been described in the context of manually selecting and adjusting the electrical current on the electrodes, it should be appreciated that these techniques are applicable to automated current steering, such that, as electrical current is steered along the electrodes, the linked electrodes are either locked to a certain current value or globally scaled.

Although the foregoing techniques have been described as being implemented in the CP 18, it should be noted that this technique may be alternatively or additionally implemented in the RC 16. Furthermore, although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system for programming a neurostimulator that is configured to deliver neurostimulation using a plurality of electrodes, the system comprising:
   a processor configured to control fractionalized electrode contributions of energy delivered using active ones of the plurality of electrodes, and
   a user interface configured to receive a user selection of at least two electrodes of the plurality of electrodes and less than all of the plurality of electrodes;

wherein the processor is configured to respond to the user selection of the at least two electrodes by linking the at least two electrodes to provide linked electrodes, the user interface is further configured to receive a user input to globally scale amplitude for the fractionalized electrode contributions of the linked electrodes, and the processor is configured to respond to the user input by changing an amount of energy delivered using the linked electrodes without changing a relative percentage between or among the fractionalized electrode contributions provided by the linked electrodes.

2. The system of claim 1, wherein the processor is further configured to compensate for the change in the amount of energy delivered using the linked electrodes by changing a fractionalized contribution for at least one other electrode in the plurality of electrodes.

3. The system of claim 1, wherein the fractionalized electrode contributions of energy include fractionalized electrode current values.

4. The system of claim 1, wherein the user selection of the at least two electrodes includes drawing a shape around the at least two electrodes to provide the linked electrodes.

5. The system of claim 1, wherein the user selection of the at least two electrodes includes at least one check box to provide the linked electrodes.

6. The system of claim 1, wherein the user selection of the at least two electrodes includes highlighting of the at least two electrodes to provide the linked electrodes.

7. The system of claim 1, wherein the linked electrodes have at least two different relative percentages.

8. A method implemented using a system for programming a neurostimulator that is configured to deliver neurostimulation using a plurality of electrodes, wherein the system includes a processor and a user interface, the method comprising:
using the processor to control fractionalized electrode contributions of energy delivered using active ones of the plurality of electrodes, and
using the user interface to receive a user selection of at least two electrodes of the plurality of electrodes and less than all of the plurality of electrodes;
using the processor to respond to the user selection of the at least two electrodes by linking the at least two electrodes to provide linked electrodes,
using the user interface to receive a user input to globally scale amplitude for the fractionalized electrode contributions of the linked electrodes, and
using the processor to respond to the user input by changing an amount of energy delivered using the linked electrodes without changing a relative percentage between or among the fractionalized electrode contributions provided by the linked electrodes.

9. The method of claim 8, further comprising using the processor to compensate for the change in the amount of energy delivered using the linked electrodes by changing a fractionalized contribution for at least one other electrode in the plurality of electrodes.

10. The method of claim 8, wherein the fractionalized electrode contributions of energy include fractionalized electrode current values.

11. The method of claim 8, wherein the user selection of the at least two electrodes includes a drawn shape around the at least two electrodes to provide the linked electrodes.

12. The method of claim 8, wherein the user selection of the at least two electrodes includes at least one selected check box to provide the linked electrodes or highlighting of the at least two electrodes to provide the linked electrodes.

13. The method of claim 8, wherein the linked electrodes have at least two different relative percentages.

14. A non-transitory machine-readable medium including instructions, which when executed by a machine, cause the machine to:
control fractionalized electrode contributions of energy delivered using active ones of the plurality of electrodes;
receive a user selection of at least two electrodes of the plurality of electrodes and less than all of the plurality of electrodes;
respond to the user selection of the at least two electrodes by linking the at least two electrodes to provide linked electrodes;
receive a user input to globally scale amplitude for the fractionalized electrode contributions of the linked electrodes, and
respond to the user input by changing an amount of energy delivered using the linked electrodes without changing a relative percentage between or among the fractionalized electrode contributions provided by the linked electrodes.

15. The non-transitory machine-readable medium of claim 14, further comprising instructions, which when executed by the machine, cause the machine to compensate for the change in the amount of energy delivered using the linked electrodes by changing a fractionalized contribution for at least one other electrode in the plurality of electrodes.

16. The non-transitory machine-readable medium of claim 14, wherein the fractionalized electrode contributions of energy include fractionalized electrode current values.

17. The non-transitory machine-readable medium of claim 14, wherein the user selection of the at least two electrodes includes a drawn shape around the at least two electrodes to provide the linked electrodes.

18. The non-transitory machine-readable medium of claim 14, wherein the user selection of the at least two electrodes includes at least one selected check box to provide the linked electrodes.

19. The non-transitory machine-readable medium of claim 14, wherein the user selection of the at least two electrodes includes highlighting of the at least two electrodes to provide the linked electrodes.

20. The non-transitory machine-readable medium of claim 14, wherein the linked electrodes have at least two different relative percentages.

* * * * *